(12) United States Patent
Boechat et al.

(10) Patent No.: US 10,065,927 B2
(45) Date of Patent: Sep. 4, 2018

(54) α-KETOACYLIC ISONIAZID COMPOUNDS, PROCESS FOR PRODUCING SAID COMPOUNDS, USE OF THE COMPOUNDS IN THE TREATMENT OF TUBERCULOSIS

(71) Applicant: FUNDAÇ ÃO OSWALDO CRUZ (FIOCRUZ), Rio de Janeiro (BR)

(72) Inventors: Núbia Boechat, Rio de Janeiro (BR); Frederico Silva Castelo Branco, Rio de Janeiro (BR)

(73) Assignee: FUNDACÃO OSWALDO CRUZ (FIOCRUZ), Rio de Janeiro (BR)

( * ) Notice: Subject to any disclaimer, the term of this patent is extended or adjusted under 35 U.S.C. 154(b) by 0 days.

(21) Appl. No.: 15/543,937

(22) PCT Filed: Jan. 14, 2016

(86) PCT No.: PCT/BR2016/000004
§ 371 (c)(1),
(2) Date: Jul. 14, 2017

(87) PCT Pub. No.: WO2016/112447
PCT Pub. Date: Jul. 21, 2016

(65) Prior Publication Data
US 2017/0369445 A1 Dec. 28, 2017

(30) Foreign Application Priority Data

Jan. 15, 2015 (BR) .............................. 102015000922

(51) Int. Cl.
*A61K 31/44* (2006.01)
*C07D 213/86* (2006.01)

(52) U.S. Cl.
CPC .................................. *C07D 213/86* (2013.01)

(58) Field of Classification Search
CPC ... C07D 213/46; C07D 213/86; C07D 213/48
See application file for complete search history.

(56) References Cited

U.S. PATENT DOCUMENTS 6,716,860 B2 * 4/2004 Lauffer ................ C07D 213/30
514/353

FOREIGN PATENT DOCUMENTS

WO    WO-2016112447 A1 *  7/2016

OTHER PUBLICATIONS

A.Catto et al., 38 Farmaco, Edizione Scientifica, 45-56 (1983).*
WO 2016112447, English Translation of International Preliminary Report on Patentability Chapter I (2017).*
F. Castelo-Branco et al., 146 European Journal of Medicinal Chemistry, 529-540 (2018).*

Albrecht, F., Synthesis and Reactions of (o-Acylamino)phenylglyoxylic Amides, Liebigs Ann. Chem. 1982, pp. 794-804.
Branco F.S., Development of Novel Gem-Difluorinated Derivatives of Isoniazid With Potent Activity Against *Mycobacterium tuberculosis*, SBA-060, The 7th Brazilian Symposium o Medicinal Chemistry (BrazMed Chem 2014), p. 5.
Hearn, Michael J., Preparation and antitubercular activities in vitro and in vivo of novel Schiff bases of isoniazid, European Journal of Medicinal Chemistry 44 (2009) pp. 4169-4178.
Brooke, Edward W., An Approach to Identifying Novel Substances of Bacterial Arylamine N-Acetyltransferases, Bioorganic & Medicinal Chemistry 11 (2003) pp. 1227-1234.
Catto, A., Antisecretory and Antiulcerogenic Activity of N-(2 Acylaminophenyl) Glyoxalyl-N'-Acylhydrazines and N-(2-Benzoylaminophanyl)Glyoxatylamides), Jan. 1983, pp. 45-56.
Branco, F.S.C., Sintese de novas α,α difluoroidrazidas como substantias prototipoa inibidoras de *Mycobacterium tuberculosis*, UFRJ, Rio de Janeiro, (2011).
Carvalho, *Synthesis and antimycobacterial evaluation of new trans-action-cinnamic acid hydrazide derivatives*, Bioorganic & Medicinal Chemistry Letters 18 (2008) pp. 538-541.
Hearn, *In vitro and in vivo activities of acylated derivatives of isoniazid against Mycobacterium tuberculosis*, Drug Design and Discovery, 18: pp. 103-108, 2003.
Hearn, *Preparation and antitubercular activities in vitro and in vivo of novel Schiff bases of isoniazid*, European Journal of Medicinal Chemistry 44 (2009) pp. 4169-4178.
Judge, *Isonicotinic acid hydrazide derivatives: synthesis, antimycobacterial, antiviral, antimicrobial activity and QSAR studies*, Letters in Drug Design & Discovery, 2011, 8, pp. 792-810.
Kumar, *Synthesis of novel 1,2,3-triazole derivatives of isoniazid and their in vitro and in vivo antimycobacterial activity evaluation*, European Journal of Medicinal Chemistry 81, (2014) pp. 301-313.
Lourenço, *Evaluation of anti-tubercular activity of nicotinic and isoniazid analogues*, ARKIVOC (2007) pp. 181-191.
Mohamad, *Susceptibility of Mycobacterium tuberculosis to isoniazid and its derivative, 1-isonicotinyl-2-nonanoyl hydrazine: investigation at cellular level*, Tuberculosis (2004) 84, pp. 56-62.
Rastogi, *Action of 1-isonicotinyl-2-Palmitoyl hydrazine against the mycobacterium avium complex and enhancement of its activity by m-Fluorophenylalanine*, Antimicrobial Agents and Chemotherapy, Nov. 1990, pp. 2061-2064.

* cited by examiner

*Primary Examiner* — Alexander R Pagano
(74) *Attorney, Agent, or Firm* — Kilpatrick Townsend & Stockton LLP

(57) ABSTRACT

The instant invention relates to compounds of formula I

Formula I

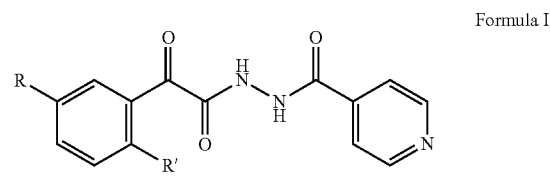

wherein: R is selected from H, Me or Cl, and R' is selected from: H, $NH_2$, $NHCOCH_3$, $NHCOCF_3$ or $NHCOCH_2Cl$. The invention further provides a process for obtaining the compounds of formula I and their use.

14 Claims, No Drawings

α-KETOACYLIC ISONIAZID COMPOUNDS, PROCESS FOR PRODUCING SAID COMPOUNDS, USE OF THE COMPOUNDS IN THE TREATMENT OF TUBERCULOSIS

FIELD OF THE INVENTION

The instant invention relates to compounds of formula I

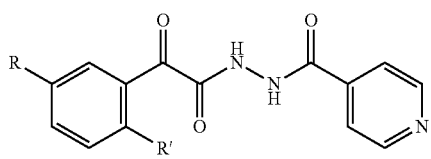

Formula I wherein:
R is selected from H, Me or Cl.
R' is selected from: H, $NH_2$, $NHCOCH_3$, $NHCOCF_3$ or $NHCOCH_2Cl$.

BACKGROUND OF THE INVENTION

Tuberculosis (TB), caused by *bacillus Mycobacterium tuberculosis* is the main infectious disease in the world. The World Health Organization (WHO) has stated that approximately 8 million of new cases are reported each year and 2 million deaths are caused by this disease. In addition, one-third of the world's population has latent *M. tuberculosis* infection, mostly in underdeveloped countries.

TB control basically consists of treating subjects diagnosed with TB with a combination of drugs, usually isoniazid (INH), rifampicin (RMP), pyrazinamide (PZA), and ethambutol (E), which are considered first-line drugs.

In Brazil, it is estimated that more than 50 million people are infected by the TB *bacillus*, and in the states of Rio de Janeiro and Amazonas the incidence rates of the disease are alarming, with figures comparable to those of India and African countries. Approximately 100 thousand new cases and 5 to 6 thousand deaths as a result of the disease are reported per year.

There is an urgent need for the development of new drugs for TB treatment, since TB first-line chemotherapy consists of drugs that were developed over 40 years ago. Due to the appearance of strains resistant to multiple chemotherapeutic agents, combined with HIV co-infection, in 1993 TB was declared as a "Global Emergency" by the WHO.

Isoniazid (INH), a prodrug inhibitor of mycolic acid synthesis, is a first choice drug for the treatment of TB because it exhibits good tolerability allied to a high antimycobacterial activity, besides being cheap. Its activation depends on the enzyme catalase-peroxidase (KatG) of *M. tuberculosis* in a hydrogen peroxide-dependent process involving the formation of the corresponding acyl radical and subsequent reaction with nicotinamide adenine dinucleotide (NAD) generating the INH-NAD adduct that inhibits the InhA enzyme involved in the synthesis of mycolic acid, constituent of the cell wall of the *bacillus*.

Two aspects are very important in the INH potency: bioavailability and lipophilic character. The importance of the lipophilicity of a compound is associated with the diffusion phenomena across the cell wall of the *bacillus*. More lipophilic compounds exhibit greater diffusion through the lipid domain, thereby increasing drug intracellular concentrations. High bioavailability, especially with high peak concentrations shortly after drug administration, increases treatment efficacy and prevents the development of INH resistance.

INH acetylation process is critical in patients of the "rapid acetylators" type, who have a higher activity of the NAT enzyme, through mutations thereof, and in this case the use of INH is not very effective, since it is converted faster to its metabolite of low activity (Selkon, J., Fox, W., Gangadharam, P., Ramachandran, K., Ramakrishnan, C., and Veiu, S., *Bull. W.H.O.*, 1961, 25, 779.). Moreover, N-acetylation may be related to mycobacterial resistance to INH in strains that overexpress the NAT enzyme (Payton, M., Auty, R., Delgoda, R., Everett, M., and Sim, E., *J. Bacteriol.*, 1999, 181, 1343.).

The prior art "Synthesis and antisecretory and antiulcerogenic activity of N-(2-acylaminophenyl)glyoxalyl-N'-acyl-hydrazines and N-(2-benzoylaminophenyl)glyoxalylamides. Catto, A.; Cappeiletti, R.; Leonardi, A.; Tajana, A.; Maggi, F.; Nardi, D.; Taddei, F, Div. Ric, Recordati S.p.A., Milan, Italy. Farmaco, Edizione Scientifica (1983), 38(1), 45-56, describes novel hydrazide compounds of similar formula, but not equal to I, however with a different production methodology. However, the authors of this scientific paper have not evaluated the compounds against *Mycobacterium tuberculosis*, especially compound II, whose structure most resembles that of I. It is noteworthy that the compound of formula I cannot be produced from II or vice-versa.

The product obtained in Catto A. et al.'s reference is compound 4

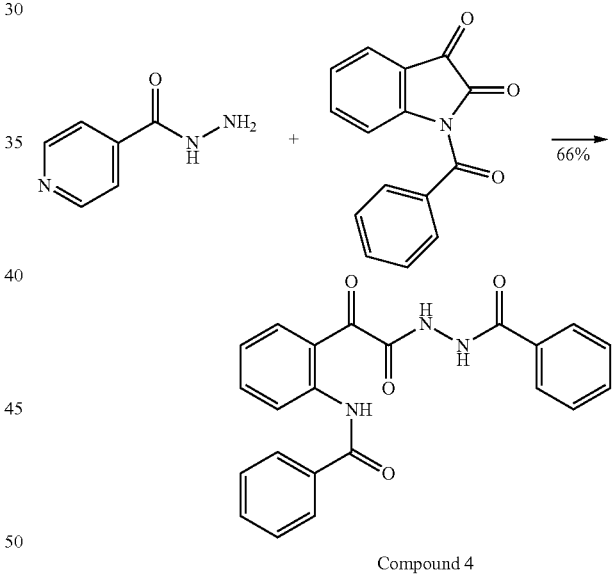

Compound 4

In order to compare the activity of substance II to the ones contained in formula I of this invention, we synthesized compound 4 and tested it against *M. tuberculosis*. Compound 4 did not show good activity and the results are shown in Table 1 and described in Examples 3 and 4

Hence, considering the high levels of resistance of the microorganism to the drugs conventionally used in the treatment of *tuberculosis*, especially isoniazid (INH), there is an urgent need for the development of new drugs useful in TB treatment.

DESCRIPTION OF THE INVENTION

The instant invention has the main objective of producing novel isoniazid (INH) derivatives with α-keto-acyl groups to promote the protection of INH against N-acetylation, in order to obtain substances with higher antimycobacterial potential in INH-susceptible and resistant strains.

The instant invention discloses novel isoniazid (INH) derivatives of formula I

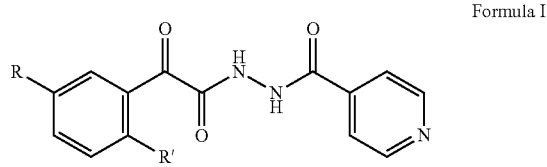

Formula I wherein:

| Compound | R | R' |
|---|---|---|
| 2 | H | NHCOCH₃ |
| 6 | CH₃ | NHCOCH₃ |
| 8 | H | NHCOCH₂Cl |
| 10 | Cl | NHCOCH₃ |
| 12 | H | NHCOCF₃ |
| 14 | CH₃ | NHCOCF₃ |
| 16 | H | NH₂ |
| 18 | H | H |

An objective of the instant invention is a process for obtaining the compounds of formula I.

Another objective of the invention relates to the use of the compounds of formula I in tuberculosis treatment.

The treatment method that uses the compounds of formula I is also an objective of the instant invention.

In the preferred embodiment, the process for obtaining the compound of formula I consists of the steps of:

(a) reacting a 5-substituted acillisatin with isoniazid in the presence of acetonitrile and water over a period of 16 hours under stirring at room temperature, followed by vacuum filtration, washing with water and ice-cold acetonitrile and air drying;

(b) reacting the corresponding isatins with acetic anhydride and sulfuric acid for 5 minutes at 140° C. followed by vacuum filtration and recrystallization with activated charcoal, ethyl acetate and hexane (1:1).

(c) reacting the chloroacetyl chloride with the corresponding isatins at reflux temperature for 16 hours followed by filtration.

(d) under anhydrous conditions and under argon atmosphere, reacting phenylglyoxylic acid chloride with isoniazid in the presence of anhydrous acetonitrile as solvent, for 16 hours at room temperature, followed by filtration and washing with water and ice-cold acetonitrile.

In the process of the instant invention, the solvent of the final reaction steps is selected from the group consisting of water and acetonitrile or dioxane or tetrahydrofuran or other polar aprotic solvent.

The invention will now be described with reference to the examples which demonstrate the preparation of the compounds incorporated by formula I. However, these examples should not be considered as limiting the scope of the instant invention. All of the obtained compounds of formula I were fully characterized by physical methods of analysis.

EXAMPLES

Organic Synthesis

The synthesis of the compounds of formula I is achieved from isatins and their 5-substituted derivatives. Isatins may be N-acetylated with the corresponding anhydrides, providing N-acetylisatins, which react with isoniazid in acetonitrile under different conditions in the presence of water to yield the final derivatives of interest [a. NARDI, D.; TAJANA, A.; PORTIOLI, F.; BOLONA, G. Farmaco, Edizione Scientifica, 37(12), 815-23; 1982/b. BOEGHAT, N.; KOVER, W. B.; BASTOS, M. M.; PINTO, A. C.; MACIEL, L C.; MAYER, L. M. U.; SILVA, F. Q.; SA, P. M.; MENDONÇA, J. S.; WARDELL, S.; ARRUDA, M. S. Journal of the Brazilian Chemical Society v. 19, p. 445-457, 2008].

Antimycobacterial Analysis

For the analysis of the antimicrobial activity the molecules from the research were submitted to preliminary tests for the detection of the antimicrobial activity against *Mycobacterium tuberculosis* by the microplate colorimetric method, Alamar Blue Assay, according to Franzblau [S. G. Franzblau, R. S. Witzig, J. C. McLaughlin, P. Torres, G. Madico, A. Hernandez, M. T. Degnan, M. B. Cook, V. K. Quenzer, R. M. Ferguson and R. H. Gilman, *J. Clin. Microbiol.* 1998, 36, 362].

Then, the determination of the minimum inhibitory concentration is performed in the screening carried out up to the concentration of 6.25 μg/mL versus strain H37Rv ATCC 27294 (American Type Culture Collection, Rockville, Md.). Compounds of the invention exhibiting inhibition at the concentration of 6.25 μg/ml are again tested for determination of the minimum concentration capable of inhibiting growth, according to Franzblau [S. G. Franzblau, R. S. Witzig, J. C. McLaughlin, P. Torres, G. Madico, A. Hernandez, M. T. Degnan, M. B. Cook, V. K. Quenzer, R. M. Ferguson and R. H. Gilman, *J. Clin. Microbiol.* 1998, 36, 362].

All compounds selected by the colorimetric method are tested in the lowest concentration by the automated method BACTEC MGIT 960-TB (Becton Dickson Corporation USA).

Compounds of the invention which exhibit pigmentation are evaluated by the Middlebrook broth dilution method 7H9 base supplemented with OADC (Difco, Detroit, Mich.) followed by counting of colonies in Middlebrook 7H11 agar medium (Difco, Detroit Mich.), after a seven day-incubation period, according to Franzblau [S. G. Franzblau, R. S. Witzig, J. C. McLaughlin, P. Tones, G. Madico, A. Hernandez, M. T. Degnan, M. B. Cook, V. K. Quenzer, R. M. Ferguson and R. H. Gilman, *J. Clin. Microbiol.* 1998, 36, 362].

Example 1

Synthesis of 1-Acetylindoline-2,3-Dione (Compound 1)

N-acetylindoline-2,3-dione can be obtained from N-acetylation of isatin with acetic anhydride, under reflux for 4 hours, providing this compound 1 in 83% yield. An optimized alternative method consists in reacting isatin with five equivalents of acetic anhydride and two drops of concentrated sulfuric acid for 5 minutes to produce the compound 1 in 95% yield. This Compound 1 was characterized by mass spectrometry coupled to gas chromatography (GC-MS), presenting a fragmentation profile compatible with its chemical structure. The melting point was consistent with the one disclosed in the literature.

In a bitubulated flask coupled to a reflux condenser, 1 g of indoline-2,3-dione, five equivalents of acetic anhydride and two drops of sulfuric acid were added. The reaction medium was kept at reflux with magnetic stirring for 5 minutes. The flask was then cooled to room temperature and taken to the freezer (−20° C.) for 12 hours. The obtained solid was washed with water and allowed to air dry. The product was recrystallized from ethyl acetate:hexane (1:1) with active charcoal. The obtained solid was filtered and washed with ice-cold hexane.

Obtained mass: 1.22 g Yield: 95%.
CG-EM: m/z 189 (11%), m/z 146 (100%), m/z 147 (22%), m/z 90 (34%), m/z 43 (45%)
Measured melting point: 141-143° C./Literature: 141° C.

Example 2

Synthesis of N-(2-(2-(2-Isonicotinoylhydrazine)-2-Oxoacetyl)Phenyl) Acetamide (Compound 2)

This derivative, Compound 2, was synthesized by reacting Compound 1 with isoniazid in acetonitrile and water for 16 hours at room temperature, yielding 68% (Scheme 2).

500 mg of 1-acetylindoline-2,3-dione (2.6 mmol), 15 ml of acetonitrile, 10 ml of distilled water and 397 mg (1.1 equivalents) of Isoniazid were added to a flask. The reaction medium was kept under stirring at room temperature for 16 hours. The resulting suspension was vacuum filtered and the solid washed 3 times with 10 mL of ice-cold acetonitrile and then with distilled water until there was no further presence of residual isoniazid (detectable by ultraviolet light in thin layer chromatography). The product was air dried and stored in an amber flask under argon atmosphere.

Compound 2 was characterized by mass spectrometry (ESi-MS (−)), $^1$H and $^{13}$C nuclear magnetic resonance, infrared spectroscopy and elemental analysis, having provided experimental data compatible with its chemical structure.

The overall yield of Compound 2 was 56%, in two steps, which makes this synthesis quite interesting and viable from the industrial point of view and also from the medicinal chemistry.

Obtained mass: 585 mg/Yield: 68%.
ESI-MS(−): m/z 325
$^1$H NMR (DMSO D6, 400 MHz, δ): 2.17 (s, 3H), 7.32 (t, J=7.7 Hz, 1H), 7.70 (t, J=7.7 Hz, 1H), 7.83 (d, J=5.2 Hz, 2H), 7.96 (d, J=7.7 Hz, 1H), 8.09 (d, J=7.7 Hz, 1H), 8.81 (d, J=5.2 Hz, 2H), 10.70 (s, 1H), 11.01 (s, 2H) ppm.
$^{13}$C NMR (DMSO D6, 100 MHz, δ): 24.42 (s), 121.16 (s), 121.39 (s), 121.93 (s), 123.37 (s), 132.62 (s), 135.29 (s), 139.08 (s), 139.50 (s), 150.58 (s), 163.50 (s), 164.07 (s), 169.20 (s), 191.53 (s) ppm.
Elemental analysis (CHN):
>Experimental: (% C) 58.93, (% H) 4.29, (% N) 17.09
>Theoretical: (% C) 58.89 (% H) 4.32, (% N) 17.17
Measured melting point: 197-199° C.

SCHEME 2-REACTION OF THE PATHWAY TO OBTAIN COMPOUND 1

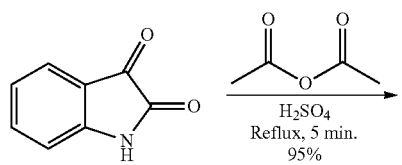

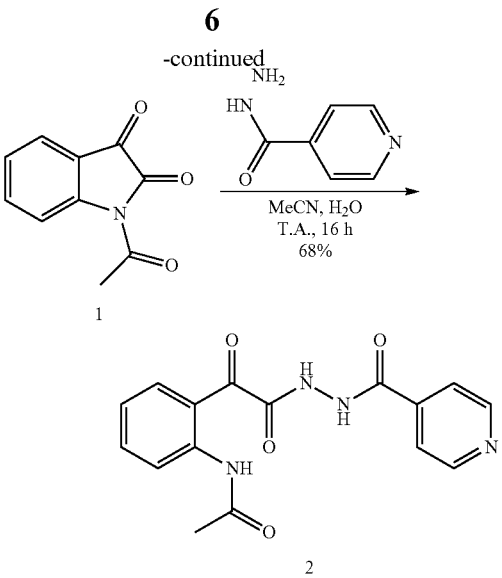

Example 3

Synthesis of 1-Benzoylindoline-2,3-Dione (Compound 3)

This compound was obtained from the reaction of isatin with benzoyl chloride in acetonitrile under reflux for 16 h with 94% yield (Scheme 3).

An amount of 500 mg (0.0034 mol) of isatin, 2 eq. of distilled benzoyl chloride, 1 mL of triethylamine and 20 mL of acetonitrile were added to a flask. The medium was kept under stirring and reflux conditions for 14 h. Then, an additional 2 eq. of benzoyl chloride was added and the reaction medium was kept under reflux for a further 4 h. The obtained precipitate was filtered and the solubilizate was concentrated in half and then left in dry ice bath with acetone for precipitation. The precipitate was washed with ice water and dried on high vacuum line.

This compound was characterized by mass spectrometry coupled to gas chromatography (GC-MS), presenting a fragmentation profile compatible with its chemical structure. The melting point was consistent with the one disclosed in the literature.

Obtained mass: 799 mg/Yield: 94%.
CG-EM: m/z 251 (17%), m/z 146 (42%), m/z 105 (100%), m/z 77 (41%), m/z 90 (11%)
Measured melting point: 160-162° C./Literature: 158-160° C.

Example 4

Synthesis of N-(2-(2-(2-Isonicotinoylhydrazinyl-2-Oxoacetyl) Phenyl) Benzamide (Compound 4)

In literature research, only one substance (4) similar to the substances proposed in this patent application was identified, obtained by Catto et al. [Catto, A.; Cappelletti, R.; Leonardi, A.; Tajana, A.; Maggi, F.; Nardi, D.; Taddei, F. *Farmaco Edizione Scientifica*, 1983, 38, 1, 45.]. However, in the literature, substance 4 was not evaluated for antimycobacterial activity, but as antiulcer in rats. In this way, this substance 4 was also synthesized and evaluated for antimycobacterial activity for comparison with the series proposed in the instant invention.

This substance was synthesized from the opening of the heterocyclic ring of compound 3 with isoniazid in acetonitrile at room temperature for 8 h (Scheme 3).

An amount of 200 mg (0.000796 mol) of 1-benzoylindoline-2,3-dione and 15 mL of MeCN were added to a flask, and the medium was kept under stirring until complete solubilization. Then, 1.1 eq. of isoniazid previously solubilized in 5 mL of water was added. The reaction medium was kept under stirring for 8 h at room temperature. The obtained precipitate was vacuum filtered and washed with ice-cold MeCN, ice-cold water and dried at high vacuum.

The obtained yield was 56% (Scheme 3). The overall yield of substance 4 was 53% and this was characterized by mass spectrometry (ESI-MS (−)) and $^1$H and $^{13}$C nuclear magnetic resonance, the data being consistent with its structure.

Obtained mass: 173 mg/Yield: 56%.

ESI-MS(−): m/z 325

$^1$H NMR (DMSO D6, 400 MHz, 5): 7.40 (t, J=7.5 Hz, 1H), 7.63 (t, J=7.3 Hz, 2H), 7.69 (t, J=7.2 Hz, 1H), 7.83 (t, J=6.5 Hz, 3H), 8.01 (d, J=7.1 Hz, 2H), 8.19 (d, J=7.0 Hz, 1H), 8.62 (d, J=8.3 Hz, 1H), 8.81 (d, J=5.3 Hz, 2H), 11.08 (s, 2H), 11.71 (s, 1H) ppm $^{13}$C NMR (DMSO D6, 100 MHz, δ): 120.18 (s), 120.87 (s), 121.34 (s), 123.44 (s), 127.23 (s), 129.01 (s), 132.43 (s), 133.80 (s), 134.02 (s), 136.35 (s), 138.92 (s), 140.74 (s), 150.52 (s), 163.75 (s), 164.08 (s), 165.22 (s), 193.36 (s).

Measured melting point: 209-211° C./Literature: 211=212° C.

SCHEME 3-REACTION OF THE PATHWAY TO OBTAIN DERIVATIVE 4

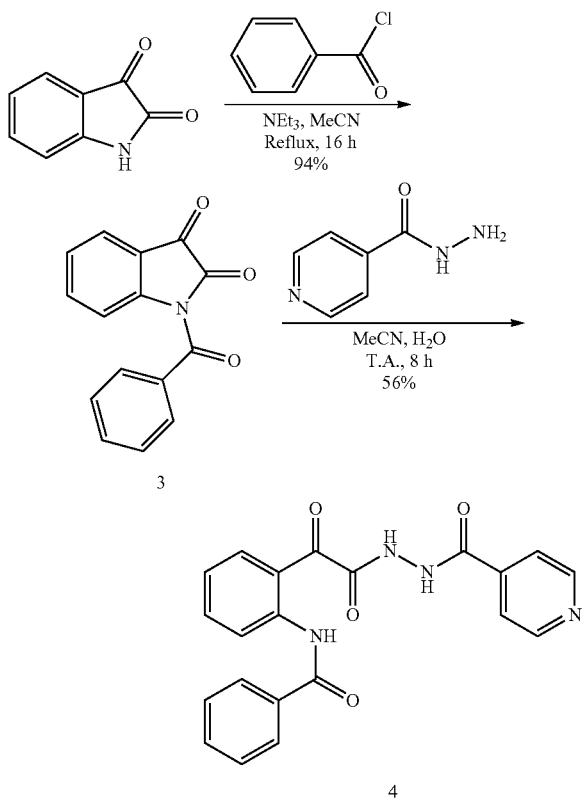

Example 5

Synthesis of 1-Acetyl-5-Methylindoline-2,3-Dione (Compound 5)

An amount of 4 g of the 5-methylindoline-2,3-dione compound and 15 equivalents of freshly distilled acetic anhydride were added to a bitubulated flask coupled to a reflux condenser. The reaction medium was kept at reflux with magnetic stirring for 4 hours. The flask was then cooled to room temperature and taken to the freezer (−20° C.) for 12 hours. The obtained solid was washed with water and allowed to air dry. The product was recrystallized from ethyl acetate:hexane (1:1) with active charcoal. The obtained solid was filtered and washed with ice-cold hexane. Product 5 was obtained with 89% yield, 4.46 g thereof being provided. Product 5 was characterized by mass spectrometry, and the fragmentation profile compatible with its structure and melting point was obtained, which was consistent with the one disclosed in the literature.

CG-EM: m/z 203 (17%), m/z 161 (52%), m/z 160 (100%), m/z 133 (21%), m/z 104 (30%), m/z 43 (27%).

Measured melting point: 172-173° C./Literature: 173° C.

Example 6

Synthesis of N-(2-(2-(2-Isonicotinoylhydrazine)-2-Oxoacetyl)-4-Methylphenyl) Acetamide (Compound 6)

Compound 6 was prepared from the reaction of 500 mg of compound 5 with 1.1 equivalent of isoniazid, using acetonitrile and water as solvents, under stirring at room temperature for 16 hours (Scheme 4). The obtained solid was vacuum filtered and washed with ice-cold acetonitrile and water, and 526 mg of compound 6 was supplied at a yield of 63%. This was characterized by mass spectrometry (ESI-MS (−)) and $^1$H and $^{13}$C nuclear magnetic resonance, the data being consistent with its structure.

ESI-MS(−): m/z 339

$^1$H NMR (DMSO D6, 400 MHz, δ): 2.14 (s, 3H), 2.37 (s, 3H), 7.52 (dd, J=8, 4, 1.6 Hz, 1H), 7.80 (d, J=1.2 Hz, 1H), 7.82 (dd, J=4.5, 1.5 Hz, 2H), 8.00 (d, J=8.4 Hz, 1H), 8.00 (d, J=8.4 Hz, 1H), 8.80 (dd, J=4.5, 1.4 Hz, 2H), 10.57 (s, 1H), 10.96 (s, 2H) ppm.

$^{13}$C NMR (DMSO D6, 100 MHz, δ): 20.20 (s), 24.33 (s), 121.23 (s), 121.37 (s), 121.86 (s), 132.51 (s), 132.65 (s), 135.83 (s), 137.21 (s), 139.10 (s), 150.53 (s), 163.59 (s), 164.13 (s), 168.97 (s), 191.67 (s) ppm.

Measured melting point: 225-226° C.

SCHEME 4-REACTION OF THE PATHWAY TO OBTAIN DERIVATIVE 6

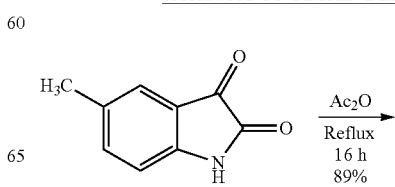

-continued

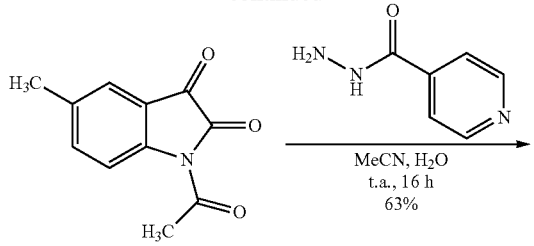

5

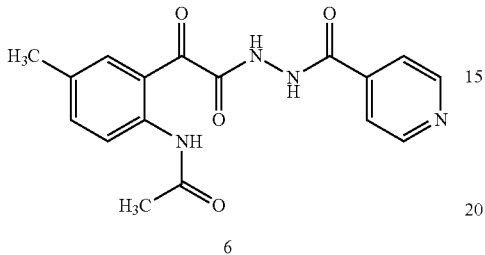

6

Example 7

Synthesis of 1-(2-Chloroacetyl) Indoline-2,3-Dione (Compound 7)

Compound 7 was prepared from 500 mg isatin using 5 ml of chloroacetyl chloride as the acylating agent and solvent. The reaction medium was kept under reflux for 16 hours and then cooled to 4° C. The formed solid was filtered and washed with hexane, providing 705 mg of product at 94% yield. Product 7 was characterized by melting point and mass spectrometry, and data consistent with the literature and its structure were provided.

CG-EM: m/z 223 (6%), m/z 197 (9%), m/z 195 (27%), m/z 147 (11%), m/z 146 (100%).

Measured melting point: 210-211° C./Literature: 210-212° C.

Example 8

Synthesis of N-(2-(2-(2-Isonicotinoylhydrazine)-2-Oxoacetyl)Phenyl) Acetamide (Compound 8)

Compound 8 was prepared from the reaction of 130 mg of compound 7 with 1.1 equivalent of isoniazid, using acetonitrile and water as solvents, under stirring at room temperature for 16 hours (Scheme 5). The obtained solid was vacuum filtered and washed with ice-cold acetonitrile and water, 135 mg of compound 8 at 65% yield being provided. This was characterized by mass spectrometry (ESI-MS (−)) and $^1$H and $^{13}$C magnetic resonance, the data being consistent with its structure.

ESI-MS(−): m/z 359

$^1$H NMR (DMSO D6, 400 MHz, δ): 11.41 (s, 1H), 11.08 (d, J=31.9 Hz, 2H), 8.81 (d, J=5.8 Hz, 2H), 8.39 (d, J=8.4 Hz, 1H), 8.13 (d, J=7.2 Hz, 1H), 7.83 (d, J=5.9 Hz, 2H), 7.79 (t, J=7.9 Hz, 1H), 7.40 (t, J=7.6 Hz, 1H), 4.51 (s, 2H).

$^{13}$C NMR (DMSO D6, 100 MHz, δ): 192.71 (s), 165.81 (s), 164.11 (s), 163.82 (s), 150.54 (s), 139.42 (S), 138.92 (S), 136.14 (S), 133.53 (S), 124.02 (S), 121.33 (s), 120.87 (s), 120.70 (s), 43.37 (s).

Measured melting point: 274-275° C.

SCHEME 5-REACTION OF THE PATHWAY TO OBTAIN DERIVATIVE 8

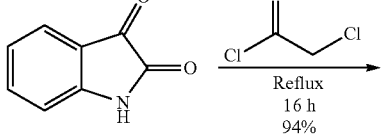

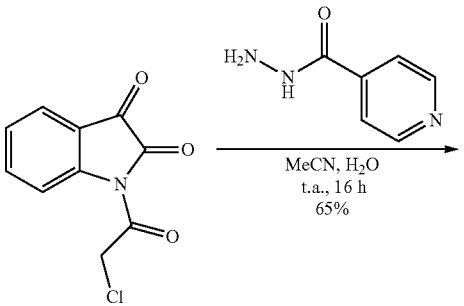

7

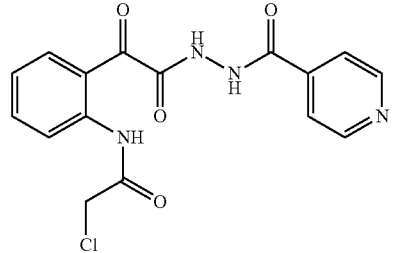

8

Example 9

Antimycobacterial Evaluation

The molecules from the research were submitted to preliminary tests for the detection of the antimicrobial activity against *Mycobacterium tuberculosis* by the microplate colorimetric dilution method, Alamar Blue Assay, according to Franzblau (FLANZBLAU et al, 1998). The determination of the minimum inhibitory concentration is performed in the screening carried out up to the concentration of 3.12 µg/mL versus strain H37Rv ATCC 27294 (American Type Culture Collection, Rockville, Md.). The compounds that demonstrate inhibition in the concentration of 3.12 µg/mL were retested to determine the lowest concentration capable of inhibiting growth. All the compounds assessed by the calorimetric method were retested at the lower concentration by the automatized method BACTEC MGIT 960-TB (Becton Dickson Corporation USA), according to all the manufacturer's recommendations.

Substances 2 and 4 were evaluated for antimycobacterial activity against the *Mycobacterium tuberculosis* strain H37Rv ATCC 27294 (American Type Culture Collection, Rockville, Md.), which is sensitive to first-choice drugs.

The evaluation was also carried out with a strain resistant to isoniazid with substance 2. Rifampicin and isoniazid were used as standard. The results are described in Table 1. The synthetic INH (2) derivative showed antimycobacterial activity superior to all the first-choice drugs in the TB treatment. It was twice as potent as isoniazid, more than three times more potent than rifampicin, more than forty times more potent than ethambutol, and almost two thousand and two hundred times more active than pyrazinamide, in strains sensitive to first-choice drugs. Furthermore, it was approximately four times more potent than isoniazid in strains resistant to it. 2-acetylisoniazide was also assessed in this experiment and, as expected, it did not show antimycobacterial activity. Moreover, compound 2 was more than twenty times more potent than compound 4.

TABLE 1

ANTIMYCOBACTERIAL EVALUATION

| | MIC(μM) | |
|---|---|---|
| Substance | M. tuberculosis strain H37Rv ATCC 27294 | M. tuberculosis isoniazid resistant strain |
| 2 | 0.37 | 19.17 |
| 4 | 8.04 | Not tested |
| Isoniazid | 0.73 | >72.99 |
| 2-acetylisomide | Inactive | Not tested |
| Rifampicin | 1.22 | 1.22 |
| Etambutol | 15.90 | Not tested |
| Pyrazinamide | 813.00 | Not tested |

Example 10

Cytotoxicity Evaluation

The cytotoxicity evaluation of compound 2 was performed with J77-4 lineage murine macrophages. This substance showed no cytotoxicity at any evaluated concentration, even at high concentration, about 270 thousand times greater than the MIC of this compound. The results of the cytotoxicity evaluation are listed in Table 2.

TABLE 2

CYTOTOXICITY EVALUATION

| Compound | Sample Concentration | Cell Viability (%) | Standard Error (%) |
|---|---|---|---|
| 2 | 100 mM | 98.2 | 1.3 |
| | 10 mM | 97.3 | 1.4 |
| | 1 mM | 97.4 | 1.3 |
| | 100 nM | 97.9 | 1.0 |
| | 10 nM | 97.8 | 1.0 |
| | 1 nM | 96.8 | 0.9 |

THE LIPINSKI'S RULE OF FIVE

The Lipinski's rule of five provides the potential for absorption and permeability of a drug candidate when the substance complies with the following requirements: molecular weight less than 500 Da, up to 10 hydrogen bond acceptors (HBA), up to 5 hydrogen bond donors (HBD), and a calculated or experimental octanol-water partition coefficient (Log Pf CLogP) less than 5 (Lipinski, C. A.; Lombardo, F.; Dominy, B. W.; Feeney, P. J. *Adv. Drug Deliv.*, 2001, 46 (1-3), 3-26).

The derivatives of formula I meet all the requirements of Lipinski's rule of five, which reinforces their potential uses in the field of antituberculosis substances. Table 3 shows compliance with the requirements of the Lipinski's rule of five for the compounds of formula T of the instant invention.

TABLE 3

DATA OF THE LIPINSKI'S RULE OF FIVE OF THE COMPOUNDS OF FORMULA I.

| | Molecular mass (Da) | HBA | HBD | CLogP |
|---|---|---|---|---|
| 2 | 326 | 8 | 3 | −3.32 |
| 6 | 340 | 8 | 3 | −1.67 |
| 8 | 374 | 8 | 3 | −2.70 |
| 10 | 360 | 8 | 3 | −1.20 |
| 12 | 380 | 9 | 3 | −2.21 |
| 14 | 394 | 9 | 3 | −0.57 |
| 16 | 284 | 8 | 4 | −3.57 |
| 18 | 269 | 6 | 2 | −1.19 |
| Lipinski's Rule of Five | <500 Da | <10 | <5 | <5 |

As shown in the results of the previous Examples, the example of derivative 2 of the instant invention:

(a) is a novel substance, cheap and easy to obtain;

(b) had higher potency than all the first-choice drugs for TB treatment in non-resistant strains of *M. tuberculosis*;

(c) was more than 20 times more potent than novel substance 4;

(D) when tested against resistant strains, was 4 times more potent than isoniazid;

(E) did not prove to be toxic in cytotoxicity tests, even in a concentration 270 thousand times greater than its MIG; and, (f) complies with the Lipinski's rule.

The invention claimed is:

1. A compound characterized by having the structure of formula I below

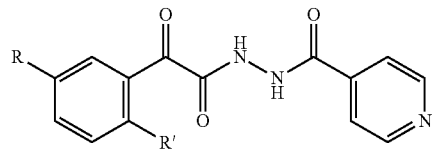

wherein:

R is selected from H, Me or Cl, and

R' is selected from: H, $NH_2$, $NHCOCH_3$ $NHCOCF_3$ or $NHCOCH_2Cl$.

2. The compound according to claim 1, wherein said compound is the compound N-(2-(2-(2-isonicotinoylhydrazinyl)-2-oxoacetyl)phenyl) acetamide (compound 2).

3. A method for producing a pharmaceutical composition for tuberculosis treatment, the method comprising using the compound having structure of formula I according to claim 1 in the pharmaceutical composition.

4. A tuberculosis treatment method wherein the treatment involves administering a therapeutically effective amount of at least one of the compounds contemplated in the structure of formula I according to claim 1.

5. A process for obtaining a compound consisting of formula I according to claim 1, the process comprising:

reacting an isatin or a 5-substituted isatin derivative with acetic anhydride and sulfuric acid followed by vacuum filtration and recrystallization with activated charcoal, ethyl acetate, and hexane to form an intermediate compound.

6. The process of claim 5, further comprising:

reacting the intermediate compound with isoniazid in the presence of a solvent, followed by vacuum filtration, washing with water and acetonitrile and air drying, to obtain the compound consisting of the structure of formula I according to claim 1.

7. The process of claim 5, wherein the intermediate product is N-acetylindoline-2,3-dione.

8. The process of claim 6, wherein the solvent is selected from the group consisting of water and acetonitrile, dioxane, tetrahydrofuran, and another polar aprotic solvent.

9. The process of claim 8, wherein the solvent is water and acetonitrile.

10. A process for obtaining a compound consisting of formula I according to claim 1, the process comprising:
   reacting chloroacetyl chloride with an isatin or a 5-substituted isatin derivative at reflux temperature followed by filtration to form an intermediate compound.

11. The process of claim 10, further comprising:
   under anhydrous conditions and under argon atmosphere, reacting the intermediate compound with isoniazid in the solvent, followed by filtration and washing with water and acetonitrile, to obtain the compound consisting of the structure of formula I according to claim 1.

12. The process of claim 10, wherein the intermediate compound is 1-(2-chloroacetyl)indoline-2,3-dione.

13. The process of claim 11, wherein the solvent is selected from the group consisting of water and acetonitrile, dioxane, tetrahydrofuran, and another polar aprotic solvent.

14. The process of claim 13, wherein the solvent is water and acetonitrile.

\* \* \* \* \*